United States Patent
Greaves et al.

(10) Patent No.: US 7,601,180 B2
(45) Date of Patent: Oct. 13, 2009

(54) USE FOR THE DYEING WITH LIGHTENING EFFECT OF KERATIN SUBSTANCES OF A COMPOSITION COMPRISING A FLUORESCENT CYANINE DYE

(75) Inventors: Andrew Greaves, Montevrain (FR); Nicolas Daubresse, La Celles St Cloud (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 12/159,949

(22) PCT Filed: Jan. 11, 2007

(86) PCT No.: PCT/EP2007/050269

§ 371 (c)(1),
(2), (4) Date: Oct. 6, 2008

(87) PCT Pub. No.: WO2007/080183

PCT Pub. Date: Jul. 19, 2007

(65) Prior Publication Data

US 2009/0049621 A1    Feb. 26, 2009

Related U.S. Application Data

(60) Provisional application No. 60/761,758, filed on Jan. 25, 2006.

(30) Foreign Application Priority Data

Jan. 12, 2006    (FR) .................................. 06 50111

(51) Int. Cl.
*A61Q 5/10* (2006.01)

(52) U.S. Cl. ...................... 8/405; 8/406; 8/407; 8/410; 8/421; 8/568; 8/648; 132/202; 132/208

(58) Field of Classification Search ...................... 8/405, 8/406, 407, 410, 421, 568, 648; 132/202, 132/208
See application file for complete search history.

(56) References Cited

U.S. PATENT DOCUMENTS

| | | | |
|---|---|---|---|
| 4,323,362 A | 4/1982 | Degent et al. | |
| 7,147,673 B2 | 12/2006 | Plos et al. | |
| 7,150,764 B2 | 12/2006 | Plos et al. | |
| 7,186,278 B2 | 3/2007 | Plos et al. | |
| 7,189,266 B2 | 3/2007 | Plos et al. | |
| 7,192,454 B2 | 3/2007 | Plos et al. | |
| 7,195,650 B2 | 3/2007 | Plos et al. | |
| 7,195,651 B2 | 3/2007 | Plos et al. | |
| 7,198,650 B2 | 4/2007 | Pourille-Grethen et al. | |
| 7,204,860 B2 | 4/2007 | Plos et al. | |
| 7,208,018 B2 | 4/2007 | Gourlaouen et al. | |
| 7,250,064 B2 * | 7/2007 | Plos et al. ...................... | 8/405 |
| 7,261,744 B2 | 8/2007 | Gourlaouen et al. | |
| 7,276,086 B2 | 10/2007 | Gourlaouen et al. | |
| 7,303,589 B2 | 12/2007 | Greaves et al. | |
| 7,377,946 B2 | 5/2008 | Gourlaouen et al. | |
| 2004/0253757 A1 | 12/2004 | Gourlaouen et al. | |
| 2005/0011018 A1 | 1/2005 | Greaves et al. | |
| 2005/0028301 A1 | 2/2005 | Pastore | |
| 2007/0231940 A1 | 10/2007 | Gourlaouen et al. | |

FOREIGN PATENT DOCUMENTS

| | | |
|---|---|---|
| EP | 1 133 975 A2 | 9/2001 |
| EP | 1 432 390 A1 | 6/2004 |
| EP | 1 464 323 A1 | 10/2004 |
| FR | 2 830 194 A1 | 4/2003 |
| FR | 2 850 271 A1 | 7/2004 |
| FR | 2 853 229 A1 | 10/2004 |
| WO | WO 03/028685 | 4/2003 |

OTHER PUBLICATIONS

STIC Search Report dated May 4, 2009.*
English language Derwent Abstract for EP 1 464 323 A1, dated 2004.
IUkrainskii Kimicheskii Zhurnal (Russ. ed.) 1980, 46(1), 81-3.
International Search Report for PCT/EP2007/050269 (PCT counterpart of U.S. Appl. No. 12/159,949), dated May 30, 2007.

* cited by examiner

*Primary Examiner*—Eisa B Elhilo
(74) *Attorney, Agent, or Firm*—Finnegan, Henderson, Farabow, Garrett & Dunner, L.L.P.

(57) ABSTRACT

The present invention relates to the use, for the dyeing with lightening effect of human keratin substances, and in particular of human keratin fibres such as the hair, of a composition comprising at least one fluorescent cyanine dye. The present invention allows human keratin substances to be both dyed and at the same time lightened without detriment to said substances. The fluorescent dyes employed in the context of the invention also have high tinctorial affinity for keratin substances and good properties of resistance towards external agents, and especially towards shampoos.

19 Claims, No Drawings

USE FOR THE DYEING WITH LIGHTENING EFFECT OF KERATIN SUBSTANCES OF A COMPOSITION COMPRISING A FLUORESCENT CYANINE DYE

CROSS REFERENCE TO RELATED APPLICATIONS

This application is a national phase application based on PCT/EP2007/050269, filed Jan. 11, 2007, which claims the priority of French Patent Application No. 0650111, filed Jan. 12, 2006, and claims the benefit of U.S. Provisional Application No. 60/761,758, filed Jan. 25, 2006, the contents of all of which are incorporated herein by reference.

The present invention relates to the use, for the dyeing with lightening effect of human keratin substances, and in particular of human keratin fibres such as the hair, of a composition comprising at least one fluorescent cyanine dye.

In the hair field, in order to obtain a lighter dyeing, it is conventional to employ a chemical bleaching method. This method consists in bleaching the melanins of the keratin fibres by an oxidizing system, which is generally composed of hydrogen peroxide in combination or not with persalts. This operation may or may not be carried out in the presence of direct dyes and/or oxidation dyes.

This bleaching system has the disadvantage of degrading the fibres and of impairing their cosmetic properties. The hair tends to become harsh, more difficult to disentangle and more fragile.

It is therefore desirable to have compositions available that allow the keratin fibres to be lightened at the same time as being dyed, aesthetically, without degrading these fibres.

The use, for the dyeing with lightening effect of human keratin substances, and in particular of human keratin fibres such as the hair, of fluorescent dyes, and in particular of 2-(2-[4-dimethylaminophenyl]vinyl)-1-ethylpyridinium, was proposed in patent application EP 1 432 390. However, the dyeings obtained are not entirely satisfactory in terms of shampoo resistance.

Patent application FR 2 853 229 describes the use, for dyeing with lightening effect human keratin substances, and in particular human keratin fibres such as the hair, of fluorescent dyes in the form of dimers, and in particular of dimers of 2-(2-[4-dimethylaminophenyl]-vinyl)-1-ethylpyridinium, the two 2-(2-[4-dimethylaminophenyl]vinyl)-1-ethylpyridinium molecules being joined to one another via a linker at the pyridinium ring. The shampoo resistance of the dyeings obtained is improved, but the lightening effect is less substantial than with 2-(2-[4-dimethylaminophenyl]vinyl)-1-ethylpyridinium.

Furthermore, cyanine compounds and their use as dyes in the paper industry have been described in U.S. Pat. No. 4,323,362.

The aim of the present invention is to provide new compositions for colouring, with lightening effect, human keratin substances, said compositions not exhibiting the disadvantages of the prior-art compositions. In particular the aim of the present invention is to provide new dyes for dyeing, with lightening effect, human keratin substances, said dyes exhibiting high tinctorial affinity for keratin substances, good properties of resistance towards external agents and in particular shampoos, and also allowing optical lightening to be obtained without impairing the substance treated.

This aim is achieved with the present invention, which provides for the use, for the dyeing with lightening effect of human keratin substances, of a composition comprising, in a cosmetically acceptable medium, at least one fluorescent cyanine dye selected from the compounds of formulae (I) or (II) below and their addition salts with an acid or a base:

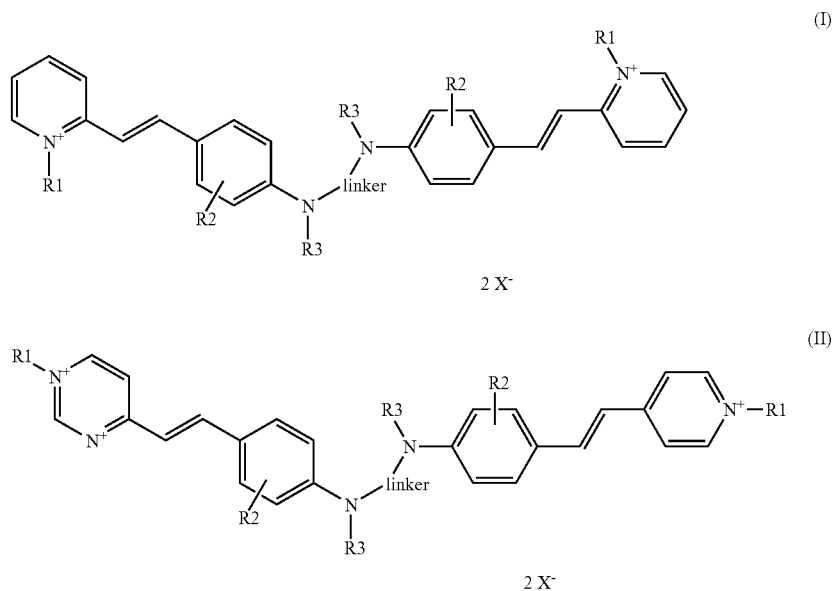

in which:

linker represents a saturated or unsaturated aliphatic or alicyclic $C_1$-$C_{12}$, preferably $C_2$-$C_8$, hydrocarbon chain, it being possible for one or more carbon atoms of the hydrocarbon chain to be replaced by one or more oxygen atoms, one or more groups NR where R is a hydrogen atom or an alkyl radical, the hydrocarbon chain containing no diazo, nitro, nitroso or peroxide group, and it not being possible for the hydrocarbon chain to be terminated at one or the other of its ends by a heteroatom;

R1 represents a linear $C_1$-$C_8$, preferably $C_1$-$C_4$, alkyl radical which is optionally substituted in terminal position by a hydroxyl radical or an alkoxy radical;

R2 represents a hydrogen atom; a halo radical; an alkyl radical; an alkoxy radical; an amino radical which is optionally substituted by one or more $C_1$-$C_4$ alkyl radicals which are themselves optionally substituted by one or more hydroxyl radicals;

R3 represents a linear $C_1$-$C_8$, preferably $C_1$-$C_4$, alkyl radical which is optionally substituted in terminal position by a hydroxyl radical or an alkoxy radical; it being possible for the two radicals R3 to form, with the linker and the nitrogen atoms to which they are attached, a 6- or 7-membered saturated heterocycle of formula:

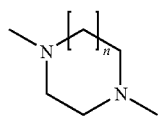

where n is 1 or 2; and

X$^-$ represents a counterion.

The present invention likewise provides a method of dyeing, with lightening effect, human keratin substances that employs the composition useful in the context of the invention.

The present invention additionally provides a multi-compartment device for implementing the method in accordance with the invention.

The present invention further provides new fluorescent cyanine dyes and also a composition for dyeing, with lightening effect, human keratin substances, comprising at least one such fluorescent dye.

The present invention further provides a composition for dyeing, with lightening effect, human keratin substances, comprising at least one fluorescent cyanine dye and at least one additive conventionally used in the field of cosmetology.

The present invention allows human keratin substances to be coloured and at the same time lightened without impairing them. In effect, in the conventional processes allowing keratin substances to be coloured and at the same time lightened, it is necessary to employ compounds which may, in the long term, give rise to damage to said substances.

More particularly the present invention makes it possible to obtain a dyeing or colouring for which the reflectance of the substances treated in accordance with the invention, when measured between 550 and 700 nm, is greater than the reflectance of the untreated substances.

The invention allows a dyeing to be obtained which is lighter than the natural colouring, with a satisfactory aesthetic effect.

Lastly, the compounds employed exhibit high tinctorial affinity for human keratin substances and good properties of resistance towards external agents, and especially towards shampoos.

According to one particular embodiment of the invention the treated keratin substances are in the form of fibres, and more particularly in the form of pigmented keratin fibres or artificially dyed fibres. These fibres are preferably hair.

Advantageously the pigmented or artificially dyed hair has a tone level of less than or equal to 6 (dark blond) and preferably less than or equal to 4 (brown).

The concept of "tone" is based on the classification of natural shades, one tone separating each shade from that immediately following or preceding it. This definition, and the classification of natural shades, is well known to styling professionals, and is published in the work "Sciences des traitements capillaires" by Charles ZVIAK 1988, Masson, pp. 215 and 278.

A fluorescent dye is for the purposes of the present invention a dye which, like any conventional dye, is a molecule which dyes by itself and absorbs light in the visible part of the spectrum and possibly in the ultraviolet region, but which, in contrast to the conventional dye, re-emits a fluorescent light in the visible spectrum, at a greater wavelength than that of the light absorbed. Appropriately, the wavelength of the light re-emitted is between 400 and 700 nm.

Unless indicated otherwise, the end points of the value ranges given below are included in those ranges.

For the purposes of the present invention, examples of a saturated aliphatic $C_1$-$C_{12}$ hydrocarbon chain include ethylene, propylene and butylene groups.

Examples of unsaturated alicyclic $C_1$-$C_{12}$ hydrocarbon chain include the group of formula:

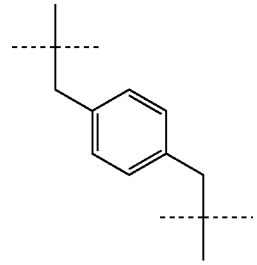

An alkyl radical (alk) is a linear or branched radical containing, unless otherwise indicated, 1 to 10 carbon atoms, preferably 1 to 6 carbon atoms, for example a methyl, ethyl, n-propyl, isopropyl, n-butyl or tert-butyl radical. An alkoxy radical is a radical alk-O—, the alkyl radical being as defined above.

Examples of linear $C_1$-$C_8$ alkyl radicals which can be substituted in terminal position by a hydroxyl radical or an alkoxy radical include 2-hydroxyethyl; 3-hydroxy-n-propyl; 4-hydroxy-n-butyl; 2-methoxyethyl; 3-methoxy-n-propyl; and 4-methoxy-n-butyl.

In the context of the present invention, a halo radical denotes a halogen atom selected from chlorine, bromine, iodine, and fluorine.

According to one particular embodiment of the invention the linker is selected from an alkylene radical and an alkylene aralkylene radical. The linker is preferably selected from an ethylene radical; a propylene radical; a butylene radical; a hexylene radical; and a group of formula:

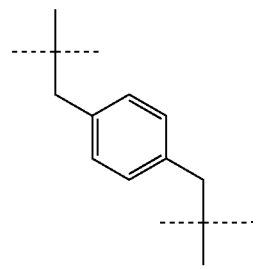

More preferably still the linker is selected from an ethylene radical; a butylene radical; and a hexylene radical.

According to another particular embodiment of the invention R1 represents an alkyl radical. R1 is preferably selected from a methyl radical and an ethyl radical.

According to another particular embodiment of the invention R2 is selected from a hydrogen atom; an alkyl radical; an alkoxy radical; and a halo radical.

R2 is preferably a hydrogen atom.

According to another particular embodiment of the invention R3 represents an alkyl radical. R3 preferably represents a methyl radical.

Examples of counterions X⁻ include halide ions such as chloride, bromide, fluoride or iodide ion, hydroxide ion, hydrogen sulphate ion, and $C_1$-$C_6$ alkyl sulphate ions such as methyl sulphate or ethyl sulphate.

Examples of compounds of formulae (I) or (II) include the compounds set out in the table below:

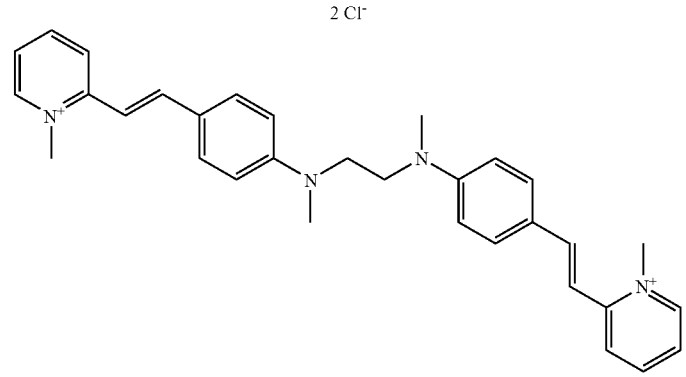

1-methyl-2-[(E)-2-(4-{methyl[2-(methyl{4-[(E)-2-(1-methylpyridinium-2-yl)vinyl]phenyl}amino)ethyl]amino}-phenyl)vinyl]pyridinium dichloride

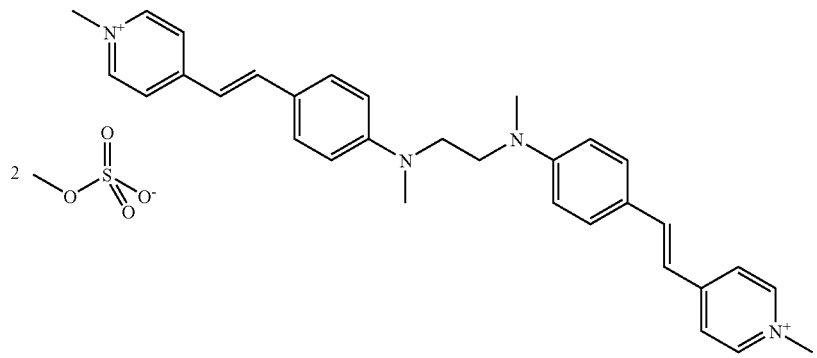

1-methyl-4-[(E)-2-(4-{methyl[2-(methyl{4-[(E)-2-(1-methylpyridinium-4-yl)vinyl]phenyl}amino)ethyl]amino}-phenyl)vinyl]pyridinium bis(methyl sulphate)

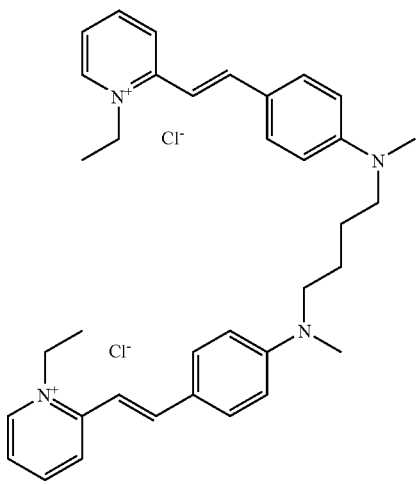

1-ethyl-2-((E)-2-{4-[{4-[{4-[(E)-2-(1-ethylpyridinium-2-yl)vinyl]phenyl}(methyl)amino]butyl}(methyl)amino]-phenyl}vinyl)pyridinium dichloride -continued

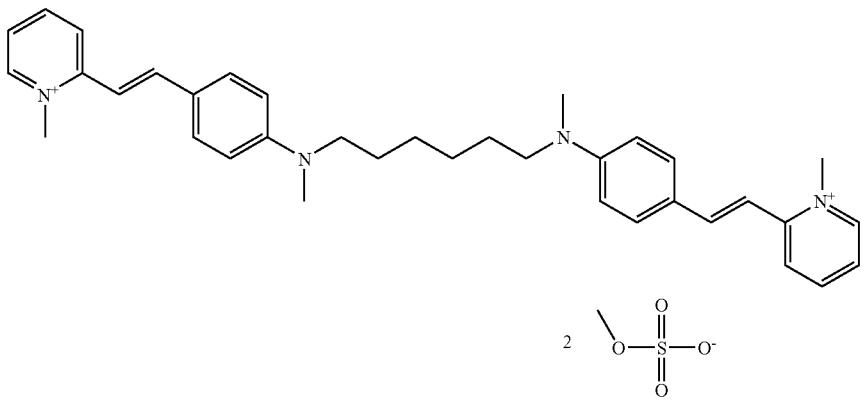

1-methyl-2-[(E)-2-(4-{methyl[2-(methyl{4-[(E)-2-(1-methylpyridinium-2-yl)vinyl]phenyl}amino)hexyl]amino}-phenyl)vinyl]pyridinium bis(methyl sulphate)

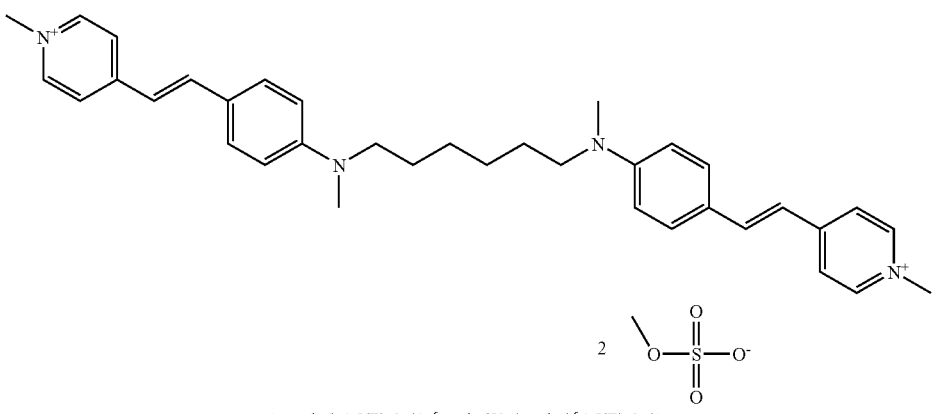

1-methyl-4-[(E)-2-(4-{methyl[2-(methyl{4-[(E)-2-(1-methylpyridinium-4-yl)vinyl]phenyl}amino)hexyl]amino}-phenyl)vinyl]pyridinium bis(methyl sulphate)

The compounds of formulae (I) or (II) which are useful in the context of the invention may for example be prepared according to the modes of synthesis as described in U.S. Pat. No. 4,323,362. They may in particular be synthesized by one of the following procedures:

Pathway 1:

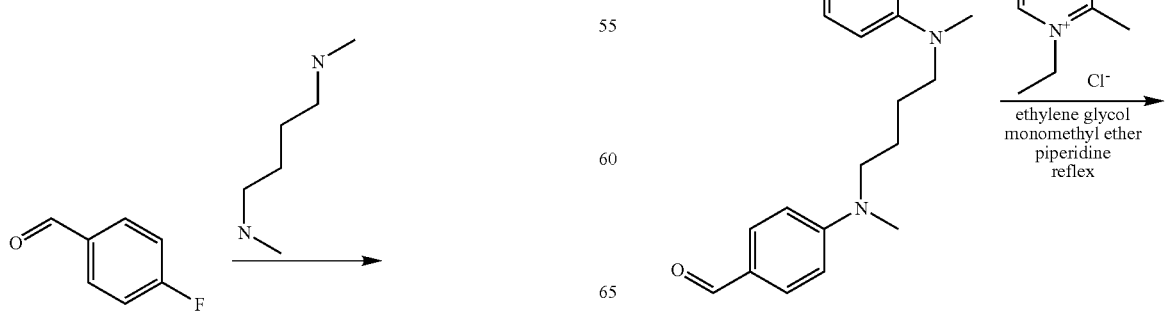

-continued

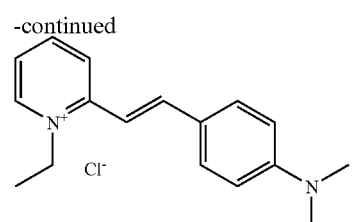

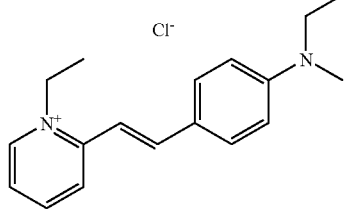

The nucleophilic substitution of a fluoro radical in an aromatic system, and in particular in 4-fluorobenzaldehyde, is described in the literature. It is possible in particular to cite the following references: Synthesis (8), 606-8, 1981 and Helvetica Chimica Acta 68(3), 584-91, 1985. Alternatives exist for this first step; for example, that described in reference JOC Section C—Organic, 7, 1966, 666-8. The condensation step is described in the following reference: J. Heterocyclic Chemistry 16(8), 1583-7, 1979.

Pathway 2:

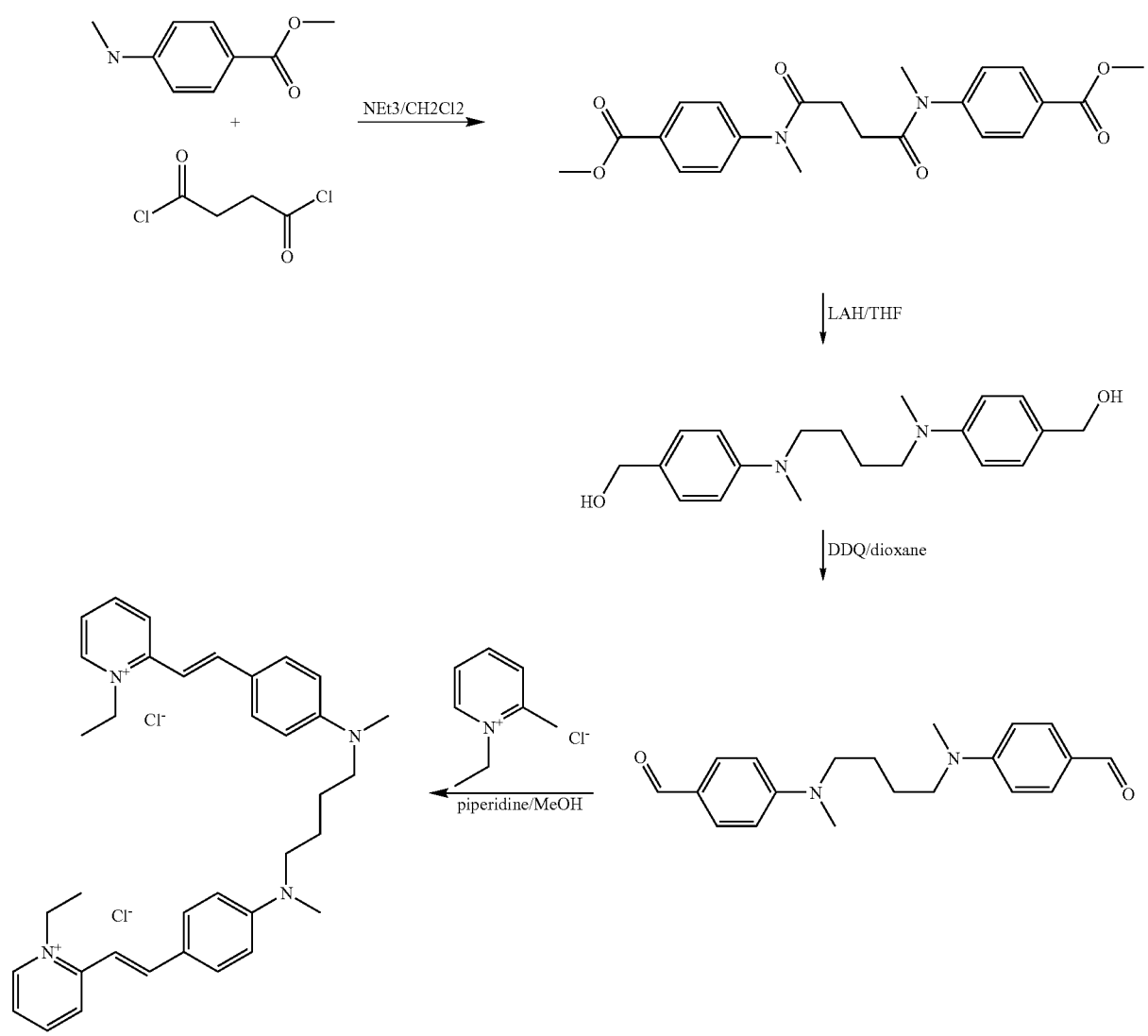

The two first synthesis steps are inspired by conditions described in the following reference: Farmaco 1989, 1167. The third synthesis step is inspired by conditions described in the following reference: J. Chem. Soc. Perkin Trans. I, 2000, 3559. The condensation step is described in the following reference: J. Heterocyclic Chemistry 16(8), 1583-7, 1979.

Pathway 3:

A particularly interesting synthesis pathway in the context of the invention is the following pathway:

The fluorescent dye or dyes which are useful in the context of the invention represent in general from 0.01% to 20% by weight relative to the total weight of the composition, more particularly from 0.05% to 10% by weight relative to the total weight of the composition, and preferably from 0.1% to 5% by weight relative to the total weight of the composition.

The cosmetically acceptable medium is generally composed of water or of a mixture of water and at least one organic solvent.

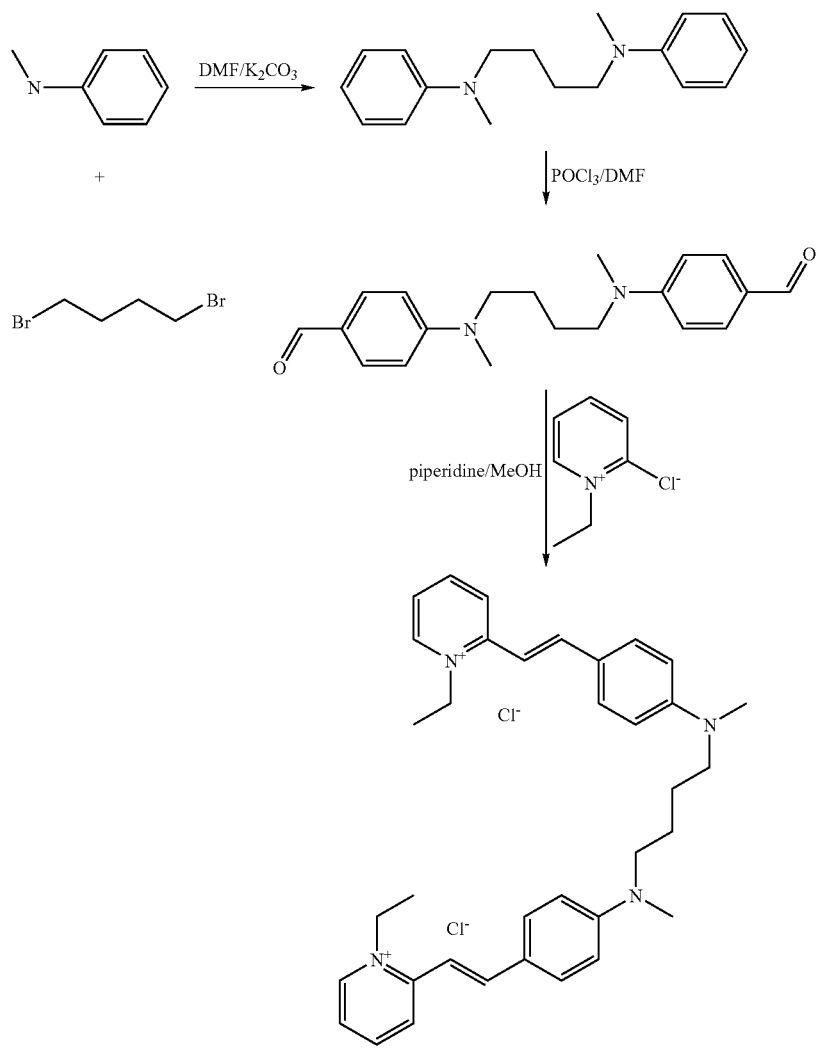

The N-alkylation reaction of an N-alkylaniline and the formulation reaction of an N,N-dialkylaniline are described, respectively, in the following references: Recueil des travaux chimiques des Pays-Bas et de la Belgique, 77, 559-568, 1958 and Organic preparations and procedures international, 36(4), 337-340, 2004. The condensation step is described in the following reference: J. Heterocyclic Chemistry 16(8), 1583-7, 1979.

In accordance with the invention, the fluorescent dye or dyes may be present in a form which is soluble or insoluble in the medium of the composition at ambient temperature (between 15 and 25° C.).

As an organic solvent mention may be made, for example, of linear or branched alkanols containing 1 to 4 carbon atoms, such as ethanol and isopropanol; polyols and polyol ethers, such as glycerol, 2-butoxyethanol, propylene glycol, propylene glycol monomethyl ether, monoethyl ether, diethylene glycol monomethyl ether, dimethoxyethane, aromatic alcohols such as benzyl alcohol or phenoxyethanol, ketones containing 3 to 4 carbon atoms, and $C_1$-$C_4$ alkyl acetates, these compounds being alone or in mixtures.

By way of illustration, the solvents, if present, represent from 1% to 40% by weight approximately relative to the total weight of the composition, and more advantageously from 5% to 30% by weight approximately relative to the total weight of the composition.

The pH of the composition which is useful in the context of the invention is generally between approximately 3 and 12, and preferably between approximately 5 and 11.

It may be adjusted to the desired value by means of acidifying or alkalifying agents which are typically used.

The acidifying agents include, by way of example, organic or inorganic acids such as hydrochloric acid, ortho-phosphoric acid, sulphuric acid, carboxylic acids such as acetic acid, tartaric acid, citric acid and lactic acid, and sulphonic acids.

Alkalifying agents include, by way of example, aqueous ammonia, alkali metal carbonates, alkanolamines such as mono-, di- and triethanolamines and derivatives thereof, sodium hydroxide or potassium hydroxide, and the compounds of formula (III) below:

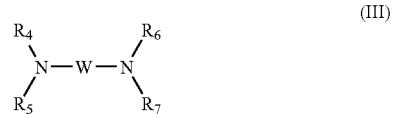

in which W is a propylene residue which is optionally substituted by a hydroxyl group or a $C_1$-$C_6$ alkyl radical; $R_4$, $R_5$, $R_6$ and $R_7$, which are identical or different, represent a hydrogen atom or a $C_1$-$C_6$ alkyl radical which optionally carries at least one hydroxyl radical.

The composition useful in the context of the present invention may further comprise one or more additional fluorescent compounds which are soluble in the medium.

Examples of a class of suitable compounds include the fluorescent compounds belonging to the following classes: naphthalimides; cationic or non-cationic coumarins; xanthenodiquinolizines (such as, in particular, sulphorhodamines); azaxanthenes; naphtholactams; azlactones; oxazines; thiazines; dioxazines; pyrenes; and nitrobenzoxadiazoles, alone or in mixtures.

More particular examples include in particular:
the compounds of structure:

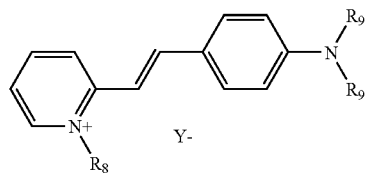

in which formula $R_8$ represents a methyl or ethyl radical, $R_9$ represents a methyl radical, and $Y^-$ represents an iodide, chloride, sulphate or methosulphate anion.

Examples of compounds of this type include Photosensitizing Dye NK-557, sold by Ubichem, for which $R_8$ represents an ethyl radical, $R_9$ a methyl radical and $Y^-$ an iodide.

Brilliant Yellow B6GL, sold by SANDOZ and having the following structure:

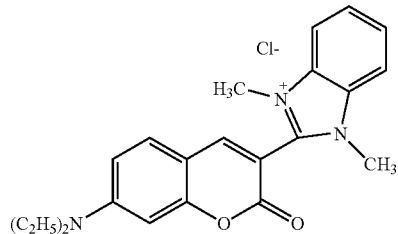

Basic Yellow 2 or Auramine O, sold by Prolabo, Aldrich or Carlo Erba and having the following structure:

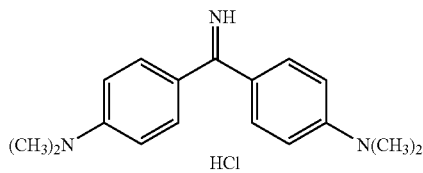

4,4'-(imidocarbonyl)bis(N,N-dimethylaniline) monohydrochloride; CAS no. 2465-27-2.

The composition useful in the context of the present invention may further comprise one or more additional fluorescent compounds which are insoluble in the medium, among which mention may be made of compounds based on zinc oxide or zinc sulphide, and also fluorescent organic compounds made from fluorescent dyes which are dissolved beforehand in a resin vehicle to give a solid which is subsequently ground.

When present in the composition useful in the context of the invention, the additional fluorescent compound or compounds represent in general from 0.05% to 10% by weight relative to the total weight of the composition, preferably from 0.1% to 5% by weight relative to the total weight of the composition.

The composition useful in the context of the invention may further comprise at least one additional, non-fluorescent, direct dye.

More particularly said additional dye is nonionic, cationic or anionic.

Generally speaking, these direct dyes are selected from nitrobenzene dyes, azo, azomethine, methine, anthraquinone, naphthoquinone, benzoquinone, phenothiazine, indigoid, xanthene, phenanthridine and phthalocyanine dyes, and those derived from triarylmethane, alone or in mixtures.

These additional direct dyes may in particular be basic dyes, among which mention may be made more particularly of the dyes known in the Colour Index, 3$^{rd}$ edition, under the names Basic Brown 16, Basic Brown 17, Basic Yellow 57, Basic Red 76, Basic Violet 10, Basic Blue 26 and Basic Blue 99, or acidic direct dyes, among which mention may be made more particularly of the dyes known in the Colour Index, 3$^{rd}$ edition, under the names Acid Orange 7, Acid Orange 24, Acid Yellow 36, Acid Red 33, Acid Red 184, Acid Black 2, Acid Violet 43 and Acid Blue 62, or else cationic direct dyes such as those described in patent applications WO 95/01772, WO 95/15144 and EP 714954, the content of which forms an integral part of the present invention.

The red or orange nitrobenzene dyes may include for example the following compounds:
1-hydroxy-3-nitro-4-N-(γ-hydroxypropyl)aminobenzene,
N-(β-hydroxyethyl)amino-3-nitro-4-aminobenzene,
1-amino-3-methyl-4-N-(β-hydroxyethyl)amino-6-nitrobenzene,
1-hydroxy-3-nitro-4-N-(β-hydroxyethyl)aminobenzene,
1,4-diamino-2-nitrobenzene,
1-amino-2-nitro-4-methylaminobenzene,
N-(β-hydroxyethyl)-2-nitro-para-phenylenediamine,
1-amino-2-nitro-4-(β-hydroxyethyl)amino-5-chlorobenzene,
2-nitro-4-aminodiphenylamine,
1-amino-3-nitro-6-hydroxybenzene,
1-(β-aminoethyl)amino-2-nitro-4-(β-hydroxyethyloxy)-benzene,
1-(β,γ-dihydroxypropyl)oxy-3-nitro-4-(β-hydroxyethyl)-aminobenzene,
1-hydroxy-3-nitro-4-aminobenzene,
1-hydroxy-2-amino-4,6-dinitrobenzene,
1-methoxy-3-nitro-4-(β-hydroxyethyl)aminobenzene,
2-nitro-4'-hydroxydiphenylamine,
1-amino-2-nitro-4-hydroxy-5-methylbenzene.

The yellow and green-yellow additional nitrobenzene direct dyes may include for example the compounds selected from:
1-β-hydroxyethyloxy-3-methylamino-4-nitrobenzene,
1-methylamino-2-nitro-5-(β,γ-dihydroxypropyl)oxy-benzene,
1-(β-hydroxyethyl)amino-2-methoxy-4-nitrobenzene,
1-(β-aminoethyl)amino-2-nitro-5-methoxybenzene,
1,3-di(β-hydroxyethyl)amino-4-nitro-6-chlorobenzene,
1-amino-2-nitro-6-methylbenzene,
1-(β-hydroxyethyl)amino-2-hydroxy-4-nitrobenzene,
N-(β-hydroxyethyl)-2-nitro-4-trifluoromethylaniline,
4-(β-hydroxyethyl)amino-3-nitrobenzenesulphonic acid,
4-ethylamino-3-nitrobenzoic acid,
4-(β-hydroxyethyl)amino-3-nitrochlorobenzene,
4-(β-hydroxyethyl)amino-3-nitromethylbenzene,
4-(β,γ-dihydroxypropyl)amino-3-nitrotrifluoromethylbenzene,
1-(β-ureidoethyl)amino-4-nitrobenzene,
1,3-diamino-4-nitrobenzene,
1-hydroxy-2-amino-5-nitrobenzene,
1-amino-2-[tris(hydroxymethyl)methyl]amino-5-nitrobenzene,
1-(β-hydroxyethyl)amino-2-nitrobenzene,
4-(β-hydroxyethyl)amino-3-nitrobenzamide.

The blue or violet additional nitrobenzene direct dyes include for example the compounds selected from:
1-(β-hydroxyethyl)amino-4-N,N-bis(β-hydroxyethyl)-amino-2-nitrobenzene,
1-(γ-hydroxypropyl)amino-4-N,N-bis(β-hydroxyethyl)-amino-2-nitrobenzene,
1-(β-hydroxyethyl)amino-4-(N-methyl-N-β-hydroxyethyl)amino-2-nitrobenzene,
1-(β-hydroxyethyl)amino-4-(N-ethyl-N-β-hydroxyethyl)-amino-2-nitrobenzene,
1-(β,γ-dihydroxypropyl)amino-4-(N-ethyl-N-β-hydroxyethyl)amino-2-nitrobenzene,
the 2-nitro-para-phenylenediamines of formula:

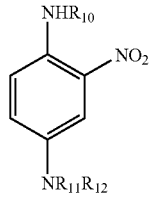

in which:
$R_{11}$ represents a $C_1$-$C_4$ alkyl radical or a β-hydroxyethyl or β-hydroxypropyl or γ-hydroxypropyl radical;
$R_{10}$ and $R_{12}$, which are identical or different, represent a β-hydroxyethyl, β-hydroxypropyl, γ-hydroxypropyl or β,γ-dihydroxypropyl radical, at least one of the radicals $R_{11}$, $R_{12}$ or $R_{10}$ representing a γ-hydroxypropyl radical, and it not being possible for $R_{11}$ and $R_{12}$ simultaneously to denote a β-hydroxyethyl radical when $R_{10}$ is a γ-hydroxypropyl radical; such as those described in French patent FR 2 692 572.

When present, the additional, non-fluorescent, direct dye or dyes represent preferably from 0.0005% to 12% by weight approximately of the total weight of the composition, and more preferably still from 0.005% to 6% by weight approximately of said weight.

The composition useful in the context of the present invention may further comprise at least one oxidation base.

The oxidation base or bases may be selected from the oxidation bases conventionally used for oxidation dyeings, such as, for example, para-phenylenediamines, bisphenylalkylenediamines, para-aminophenols, ortho-aminophenols and heterocyclic bases and their addition salts with an acid or a base.

Among the para-phenylenediamines, mention may be made more particularly, by way of example, of para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)-amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine and 4'-aminophenyl-1-(3-hydroxy)pyrrolidine, and their addition salts with an acid or a base.

Among the bisphenylalkylenediamines mention may be made more particularly, by way of example, of N,N'-bis(β-hydroxyethyl)-N,N'-bis(4'-aminophenyl)-1,3-diaminopropanol, N,N'-bis(β-hydroxyethyl)-N,N'-bis(4'-aminophenyl) ethylenediamine, N,N'-bis(4-aminophenyl) tetramethylenediamine, N,N'-bis(β-hydroxyethyl)-N,N'-bis(4-aminophenyl)tetramethylenediamine, N,N'-bis(4- methylaminophenyl)tetramethylenediamine, N,N'-bis(ethyl)-N,N'-bis(4'-amino-3'-methylphenyl) ethylenediamine, 1,8-bis(2,5-diaminophenoxy)-3,5-dioxaoctane, and their addition salts with an acid or a base.

Among the para-aminophenols mention may be made more particularly, by way of example, of para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol and their addition salts with an acid or a base.

Among the ortho-aminophenols mention may be made, for example, of 2-aminophenol, 2-amino-5-methylphenol, 2-amino-6-methylphenol, 5-acetamido-2-aminophenol, and their addition salts with an acid or a base.

Among the heterocyclic bases mention may be made in particular of pyridine derivatives, pyrimidine derivatives and pyrazole derivatives and their addition salts with an acid or a base.

The oxidation base or bases, if present, represent generally from 0.0005% to 12% by weight relative to the total weight of the composition, and preferably from 0.005% to 6% by weight relative to the total weight of the composition.

If the composition useful in the context of the invention comprises one or more oxidation bases, it may also comprise at least one coupler so as to modify or enrich with glints the shades obtained employing the fluorescent dye or dyes and the oxidation base or bases.

The couplers which can be used may be selected from the couplers used conventionally in this field, among which mention may be made in particular of meta-phenylenediamines, meta-aminophenols, meta-diphenols, heterocyclic couplers and their addition salts with an acid or a base.

These couplers are more particularly selected from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one, 1-phenyl-3-methylpyrazol-5-one, 2,6-dimethylpyrazolo-[1,5-b]-1,2,4-triazole, 2,6-dimethylpyrazolo[3,2-c]-1,2,4-triazole, 6-methylpyrazolo[1,5-a]benzimidazole, and their addition salts with an acid or a base.

When present, the coupler or couplers represent in general from 0.0001% to 10% by weight relative to the total weight of the composition, and more particularly from 0.005% to 5% by weight relative to the total weight of the composition.

Generally speaking, the addition salts with an acid that can be used in the context of the invention (fluorescent dyes of formulae (I) or (II), oxidation bases and couplers) are selected in particular from hydrochlorides, hydrobromides, sulphates, citrates, succinates, tartrates, tosylates, benzenesulphonates, lactates and acetates.

The addition salts with a base that can be used in the context of the invention (fluorescent dyes of formulae (I) or (II), oxidation bases and couplers) are selected in particular from the addition salts with alkali metals or alkaline earth metals, with aqueous ammonia, with organic amines, including alkanolamines, and the compounds of formula (III).

The composition useful in the context of the present invention may include at least one oxidant.

The oxidant is selected for example from hydrogen peroxide, urea peroxide, alkali metal bromates, persalts such as perborates and persulphates, and enzymes such as two-electron or four-electron oxidoreductases and peroxidases. The use of hydrogen peroxide or enzymes is particularly preferred.

If present, the amount of oxidant represents in general from 0.001% to 10% by weight relative to the total weight of the composition.

The composition useful in the context of the invention may further comprise various adjuvants which are conventionally used in the field of cosmetology, such as anionic, cationic, nonionic, amphoteric and zwitterionic surfactants or mixtures thereof, anionic, cationic, nonionic, amphoteric and zwitterionic polymers or mixtures thereof, organic or inorganic thickeners, and especially associative nonionic, anionic, cationic or amphoteric polymers, antioxidants, penetrants, sequestrants, perfumes, buffers, dispersants, conditioning agents such as cations, for example, cationic or amphoteric polymers, modified or non-modified, volatile or non-volatile silicones, chitosans or chitosan derivatives, film formers, ceramides, preservatives, stabilizers and opacifiers.

The adjuvants above are generally present each in an amount between 0.01% and 40% by weight relative to the weight of the composition, preferably between 0.1% and 20% by weight relative to the weight of the composition.

The person skilled in the art will of course ensure that this or these optional additional compounds are selected such that the advantageous properties intrinsically attached to the composition are not, or not substantially, impaired by the addition or additions envisaged.

The composition useful in the context of the invention may take various forms, such as lotions, shampoos, creams, gels, pastes, or any other appropriate form.

The method of dyeing, with lightening effect, keratin substances in accordance with the present invention is a method wherein a composition comprising, in a cosmetically acceptable medium, at least one fluorescent cyanine dye as defined above is applied to the keratin substances, this application being optionally followed by rinsing.

The composition applied to the keratin substances may comprise at least one additional fluorescent dye and/or at least one additional, non-fluorescent, direct dye, as have been defined above.

The composition applied to the keratin substances may also comprise at least one oxidation base and optionally at least one coupler, as have been defined above.

The composition applied to the keratin substances may be applied in the presence of at least one oxidant.

The oxidant may be added to the composition useful in the context of the invention at the time of use, or it may be employed from an oxidizing composition containing it, which is applied simultaneously or sequentially to the dyeing composition.

The oxidant is selected for example from hydrogen peroxide, urea peroxide, alkali metal bromates, persalts such as perborates and persulphates, and enzymes such as two-electron or four-electron oxidoreductases and peroxidases. The use of hydrogen peroxide or enzymes is particularly preferred.

The time needed for the dyeing to develop and for the lightening effect to obtained on the keratin fibres is generally approximately 5 to 60 minutes and more particularly approximately 5 to 40 minutes.

Moreover, the temperature required for the development of the dyeing and the obtaining of the lightening effect on the keratin fibres is generally between ambient temperature (15 to 25° C.) and 80° C. and more particularly between 15 and 40° C.

The present invention further provides a multi-compartment device which allows the method of dyeing with lightening effect, in accordance with the invention, to be implemented, when the dyeing composition is applied in the presence of an oxidant.

The multi-compartment device of the invention contains in a first compartment a composition comprising, in a cosmetically acceptable medium, at least one fluorescent cyanine dye as defined above and optionally at least one additional fluorescent dye and/or at least one non-fluorescent direct dye and/or at least one oxidation base and/or at least one coupler as defined above and in a second compartment a composition comprising at least one oxidant.

The multi-compartment device in accordance with the invention may be equipped with a means allowing the desired mixture to be delivered to the hair, such as the devices described in patent FR 2 586 913.

The present invention further provides the fluorescent dyes of formulae (I) or (II) as defined above, with the exception of 4,4'-{piperazine-1,4-diylbis[4,1-phenyleneethene-2,1-diyl]}bis(1-methylpyridinium) bis(methyl sulphate) of formula:

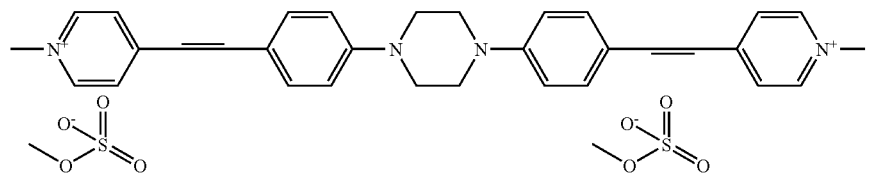

and of 4,4'-{1,4-phenylenebis[methylene(ethylimino)-4,1-phenyleneethene-2,1-diyl]}bis(1-methylpyridinium) bis(methyl sulphate) of formula:

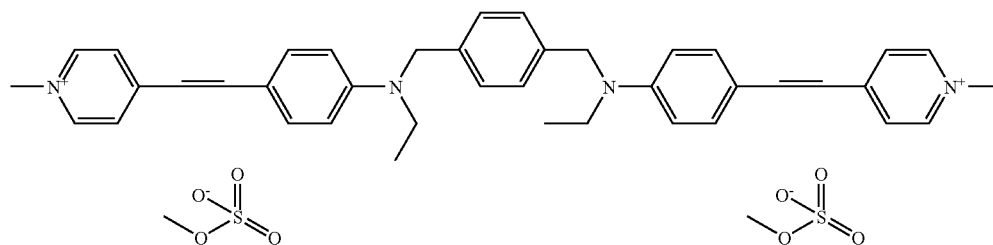

and their addition salts with an acid or a base.

Additionally provided by the present invention is a composition for dyeing, with lightening effect, human keratin substances, comprising, in a cosmetically acceptable medium, at least one fluorescent dye selected from fluorescent dyes of formulae (I) or (II) as defined above, with the exception of 4,4'-{piperazine-1,4-diylbis[4,1-phenyleneethene-2,1-diyl]}-bis(1-methylpyridinium) bis(methyl sulphate) and of 4,4'-{1,4-phenylenebis[methylene(ethylimino)-4,1-phenyleneethene-2,1-diyl]}bis(1-methylpyridinium) bis(methyl sulphate), and their addition salts with an acid or a base.

The present invention also provides a composition for dyeing, with lightening effect, human keratin substances, comprising, in a cosmetically acceptable medium, at least one fluorescent dye selected from the compounds of formulae (I) or (II) and their addition salts with an acid or a base as defined above and at least one additive selected from anionic, cationic, nonionic, amphoteric and zwitterionic surfactants and organic or inorganic thickeners, and especially nonionic, anionic, cationic or amphoteric associative polymers.

The examples which follow serve to illustrate the invention, though without having any limitative character.

EXAMPLES

Synthesis Examples

Dye 1:

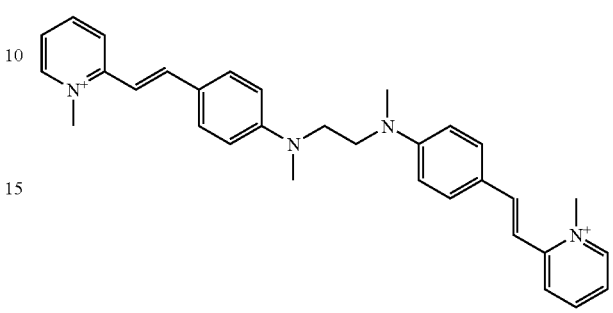

Synthesis Scheme

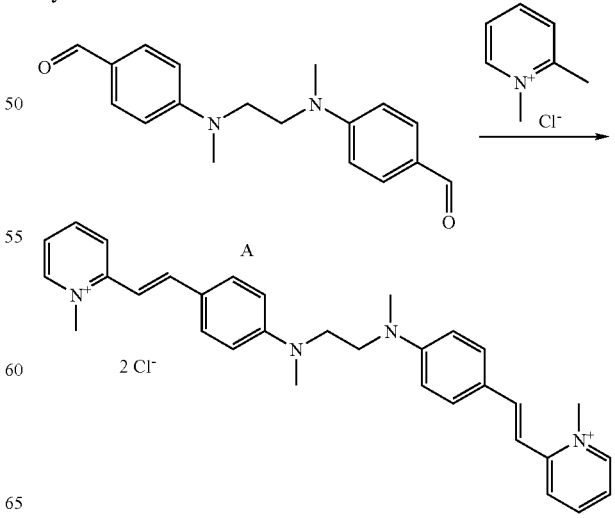

Dye 1

2.8 g of 1,2-dimethylpyridinium chloride, 50 ml of methanol and 1.4 g of pyrrolidine are introduced into a three-necked round-bottomed flask. 2.9 g of bisaldehyde A are added to this mixture and the reaction mixture is brought to reflux with stirring for 8 hours. The yellow solution obtained is then cooled to ambient temperature and subsequently poured into 300 ml of ethyl acetate. The mixture is filtered and the solid obtained is washed with ethyl acetate and then dried under vacuum. 2 g of an orange powder are recovered. Analyses indicate that dye 1 has indeed been obtained.

Dye 2:

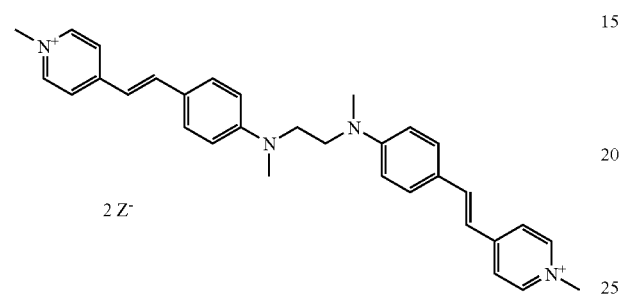

2 Z⁻

Synthesis Scheme

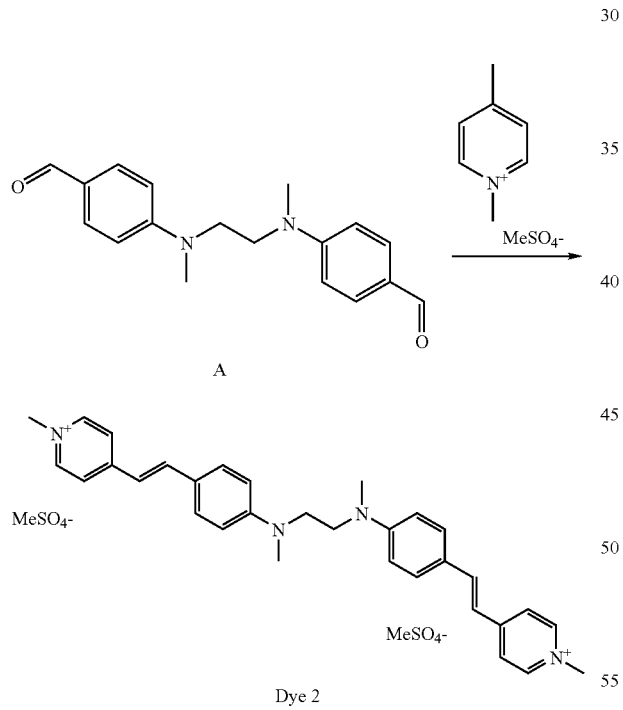

2.19 g of 1,4-dimethylpyridinium methosulphate, 25 ml of methanol and 0.7 g of pyrrolidine are introduced into a three-necked round-bottomed flask. 1.45 g of bisaldehyde A are added to this mixture and the reaction mixture is brought to reflux with stirring for 4 hours. The yellow solution obtained is then cooled to ambient temperature and filtered, and then the solid obtained is dried under vacuum. 2 g of orange crystals are recovered. Analyses indicate that dye 2 has indeed been obtained.

Dye 3:

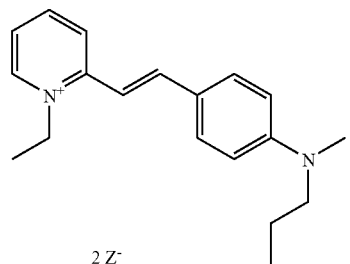

2 Z⁻

Synthesis Scheme:

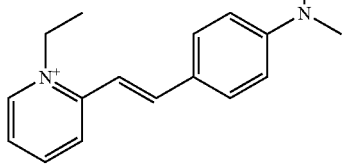

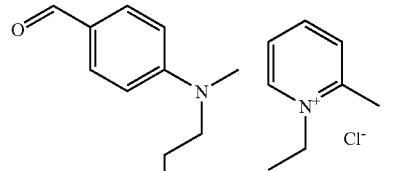

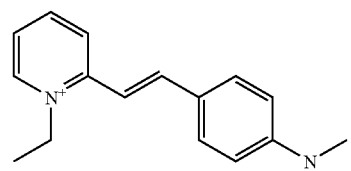

2Cl⁻

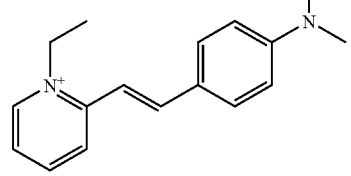

Dye 3

A solution of 3.7 g of N-ethylpicolinium in 29 ml of methanol is admixed with 3.6 g of dialdehyde C and then 2.2 ml of piperidine. The reaction mixture is refluxed with stirring for 3 hours. Diethyl ether is then poured into the reaction mixture to give a precipitate, and the mixture is placed at −20° C. overnight. The precipitate is centrifuged, the supernatant is separated and the red powder is dried. 7 g of product are recovered, and this product is purified by column chromatography (silica: methanol/water/acetic acid 8/1/1). 4.05 g of purified product are obtained in the form of scarlet red powder. Analyses indicate that dye 3 has indeed been obtained. In particular, the results of ¹H NMR analysis (D$_2$O) are as follows:

1.6 ppm, m, 10H, 3.05 ppm, s, 6H, 3.5 ppm, m, 4H, 4.7 ppm, dd, 4H, 6.7 ppm, d, 4H, 7.2 ppm, d, 2H, 7.7 ppm, m, 6H, 7.9 ppm, d, 2H, 8.3 ppm, m, 4H, 8.7 ppm, d, 2H.

Dye 4:

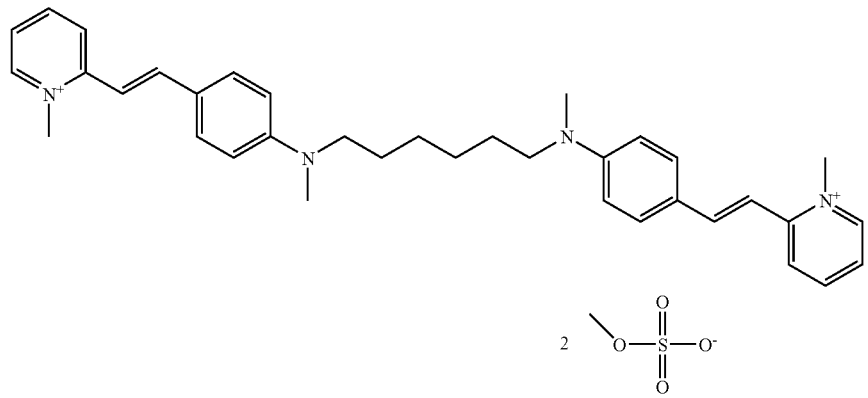

Synthesis Scheme:

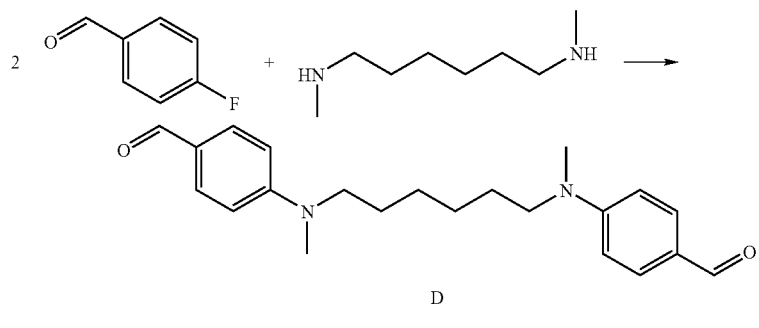

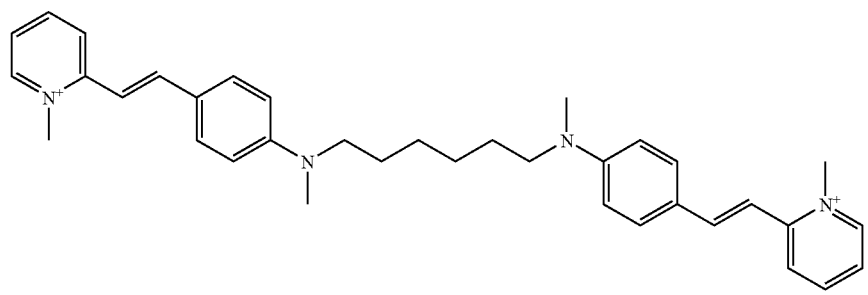

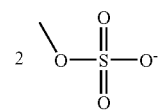

First Step 26.77 g of fluorobenzaldehyde, 100 ml of N-methylpyrrolidinone (NMP) and then 34.5 g of potassium carbonate and 14.12 g of N,N'-dimethyl-1,6-hexylenediamine are mixed and heated at 90° C. for 30 hours. The reaction mixture is cooled and poured onto 500 ml of water. The precipitate formed is washed three times with 100 ml of water and dried under vacuum. 32.9 g of pale yellow powder are collected.

Second Step 5.95 g of 2-picoline are diluted in 50 ml of dichloromethane. 6.2 ml of dimethyl sulphate are added to the mixture, which is then heated at 45° C. for 2 hours. 50 ml of isopropanol are added and the mixture is heated at 40° C. for 30 minutes. The dichloromethane is removed by distillation. 4.04 g of pyrrolidine and then 3.41 g of acetic acid are added, followed by 10 g of bisaldehyde D, obtained in the preceding step, and 20 ml of isopropanol. After three days at ambient temperature, the mixture is purified by water/butanol liquid/liquid extraction. 5.7 g of red powder are collected. Analyses confirm the nature of the expected product, particularly the results of $^1$H NMR analysis (D$_2$O).

Dye 5:

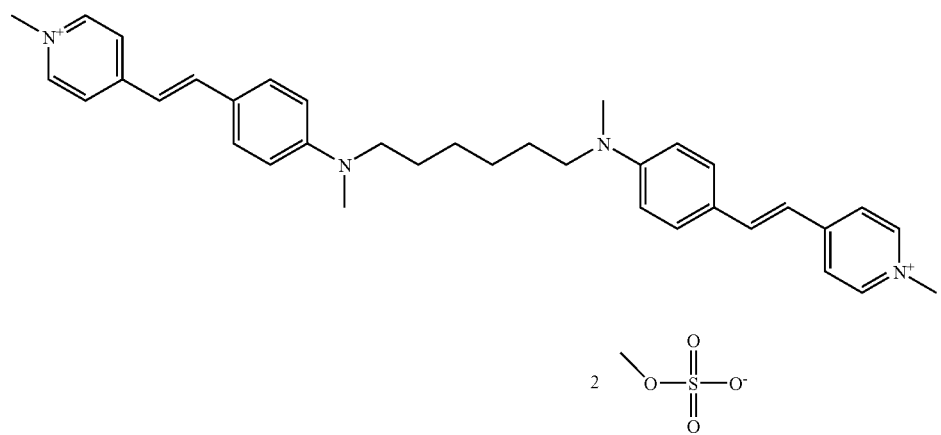

Synthesis Scheme:

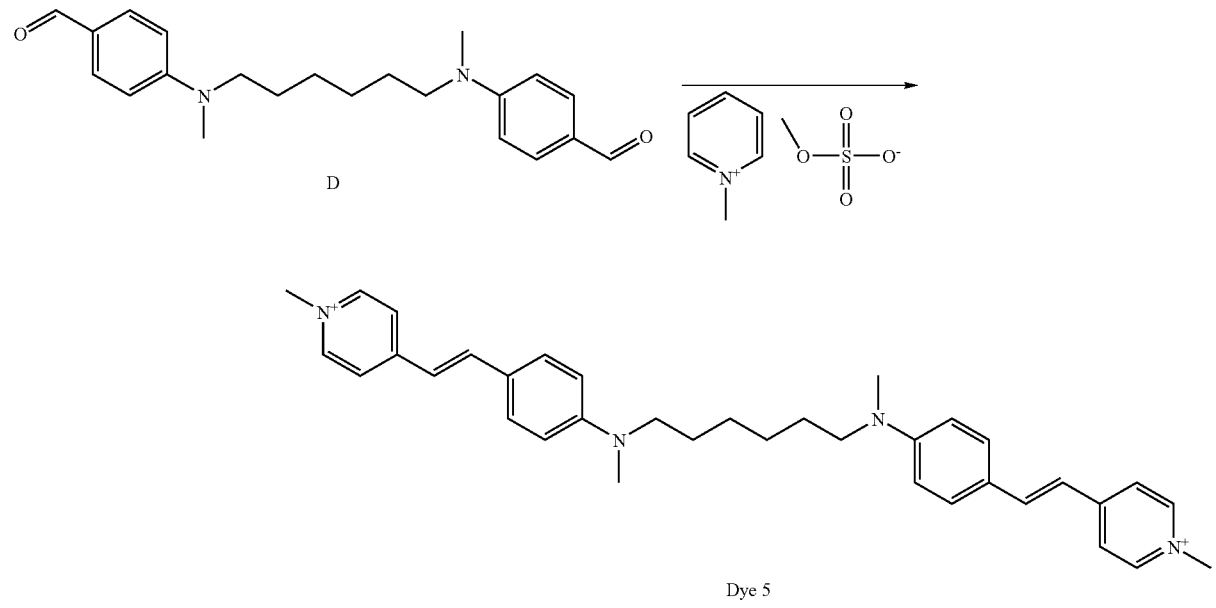

Dye 5

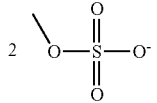

2.78 g of 4-picoline are diluted in 25 ml of dichloromethane. 3 ml of dimethyl sulphate are added to the mixture, which heats up to reflux of the dichloromethane. After 15 minutes of stirring, 50 ml of isopropanol are added and the dichloromethane is removed by distillation. 2.02 g of pyrrolidine are added, followed by 5 g of bisaldehyde D, obtained in the first step of the synthesis of dye 4, and 20 ml of isopropanol. After 2 hours of stirring at 85° C., the mixture is cooled. The precipitate formed is filtered off and washed three times with 100 ml of isopropanol, and is dried under vacuum in the presence of $P_2O_5$. 9.63 g of red powder are harvested. Analyses confirm the nature of the expected product, particularly the results of $^1H$ NMR analysis ($D_2O$).

Examples of Dyeing with Lightening Effect

Example 1

The following compositions are prepared, i being 3 or 6:

| Constituent | Composition i |
| --- | --- |
| Dye i | $10^{-3}$ mol % |
| Hydroxyethylcellulose Natrosol 250 MR | 0.36 g |
| Alkyl $C_8/C_{10}$ (50/50) hydroxyethylcellulose Oramix CG110 | 2.5 g |
| Benzyl alcohol | 2 g |
| Polyethylene glycol 400 | 2 g |
| Water | qs 100 g |

The dyes are given below.

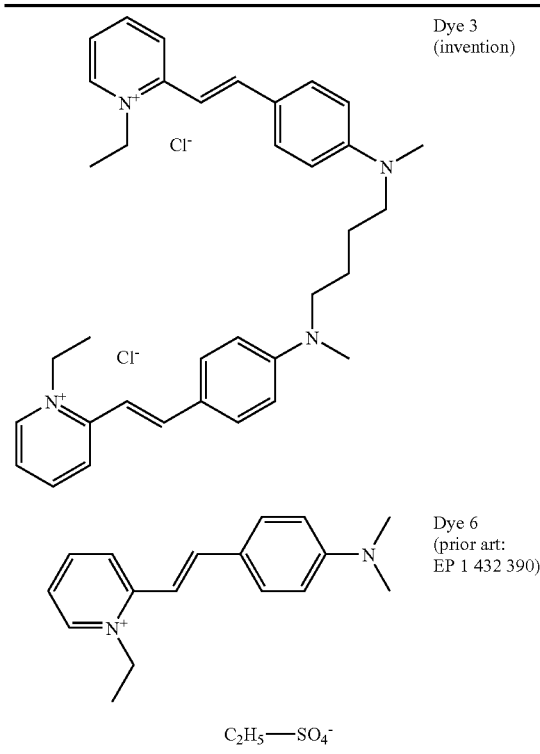

Dye 3 (invention)

Dye 6 (prior art: EP 1 432 390)

The compositions are applied to locks of natural brown hair with a tone level of 4 and to locks of natural 90% white hair, at a rate of 5 g of composition to 1 g of hair, at ambient temperature for 30 minutes. The locks are subsequently rinsed without shampoo, then dried under a hood for 30 minutes.

The results obtained are given in the table below.

| | Lock of natural brown hair (TL = 4) | Lock containing 90% natural white hair |
| --- | --- | --- |
| Dyed with dye 3 | Matt copper colour | Vivid orange |
| Dyed with dye 6 | Matt copper colour | Vivid orange |

It is noted that the dyeing obtained with the dye in accordance with the invention is visible on the hair, the same as that obtained with the dye described in patent application EP 1 432 390.

A shampoo resistance test was carried out on the locks of hair dyed with dyes 3 and 6 obtained under the conditions described above. The dyed locks were subjected to 6 shampooings in a cycle which includes the wetting of the locks with water, washing with shampoos, rinsing with water and subsequent drying.

After 6 shampooings, the dyeing obtained with dye 3 is more visible than the dyeing obtained with dye 6. These results show that the dye in accordance with the present invention exhibits better shampoo resistance than the dye described in patent application EP 1 432 390.

Example 2

The following compositions are prepared, i being 4 or 5:

| Constituent | Composition i |
| --- | --- |
| Dye i | $10^{-3}$ mol % |
| Hydroxyethylcellulose Natrosol 250 MR | 0.36 g |
| Alkyl $C_8/C_{10}$ (50/50) hydroxyethylcellulose Oramix CG110 | 2.5 g |
| Benzyl alcohol | 2 g |
| Polyethylene glycol 400 | 2 g |
| Water | qs 100 g |

The dyes are given below.

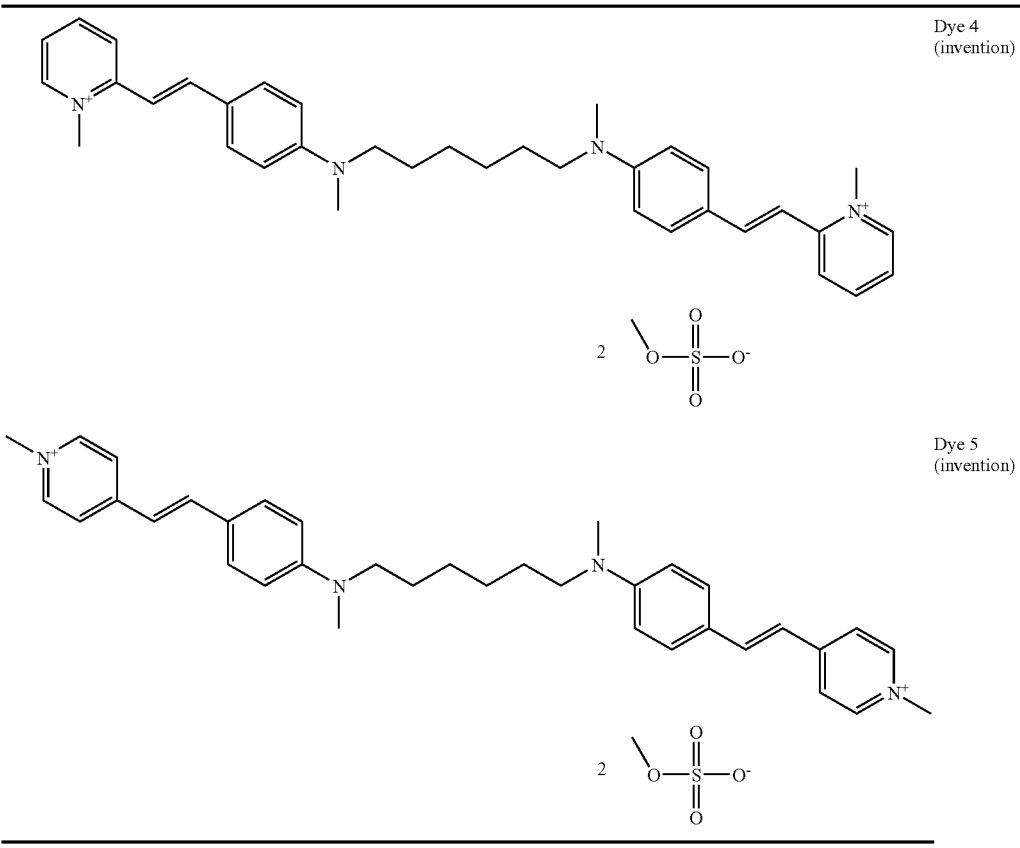

The compositions are applied to natural brown locks with a tone level of 4 and to locks of natural 90% white hair, at a rate of 5 g of composition to 1 g of hair, at ambient temperature for 30 minutes. The locks are subsequently rinsed without shampoo, then dried under a hood for 30 minutes.

The results obtained are given in the table below.

|  | Lock of natural brown hair (TL = 4) | Lock containing 90% natural white hair |
|---|---|---|
| Dyed with dye 4 | Matt copper colour | Orange |
| Dyed with dye 5 | Mahogany copper colour | Orange-red |

A shampoo resistance test was carried out on the locks of hair dyed with dyes 4 and 5 obtained under the conditions described above. The dyed locks were subjected to 6 shampooings in a cycle which includes the wetting of the locks with water, washing with shampoos, rinsing with water and subsequent drying.

The results obtained show that dyes 4 and 5 in accordance with the present invention exhibits a good shampoo resistance.

The invention claimed is:

1. A method for dyeing and lightening human keratin substances, comprising applying to the human keratin substances at least one composition for dyeing human keratin substances with lightening effect, comprising, in a cosmetically acceptable medium, at least one fluorescent cyanine dye chosen from compounds of formula (I), compounds of formula (II), and salts thereof:

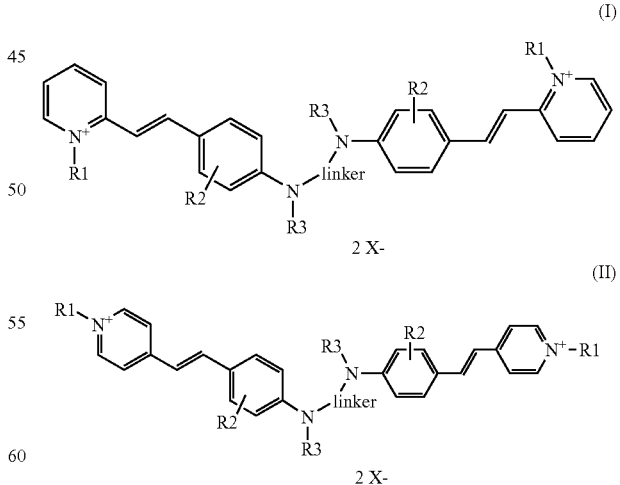

wherein:
linker represents a saturated or unsaturated, aliphatic or alicyclic $C_1$-$C_{12}$ hydrocarbon chain, wherein at least one of the carbons of the hydrocarbon chain is optionally replaced by at least one entity chosen from oxygen and NR wherein R is hydrogen or an alkyl, and further wherein the hydrocarbon chain comprises no diazo, nitro, nitroso, or peroxide groups, and the hydrocarbon chain terminates at at least one end with a carbon atom;

R1 represents a linear $C_1$-$C_8$ alkyl optionally substituted in a terminal position by hydroxy or alkoxy;

R2 represents hydrogen; halo; alkyl; alkoxy; amino optionally substituted by at least one $C_1$-$C_4$ alkyl optionally substituted by at least one hydroxyl;

R3 represents a linear $C_1$-$C_8$ alkyl optionally substituted in a terminal position by hydroxyl or alkoxy;

or two R3 form, together with the linker and the nitrogens to which they are attached, a 6- or 7-membered saturated heterocycle of formula:

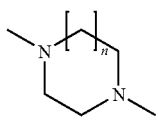

wherein n is 1 or 2; and
$X^-$ represents a counterion.

2. The method according to claim 1, wherein the linker is chosen from alkylene and alkylene aralkylene.

3. The method according to claim 1, wherein the linker is chosen from ethylene; propylene; butylene; hexylene; and groups of formula:

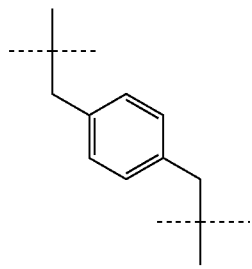

4. The method according to claim 1, wherein the at least one fluorescent cyanine dye is chosen from the compounds below and salts thereof:

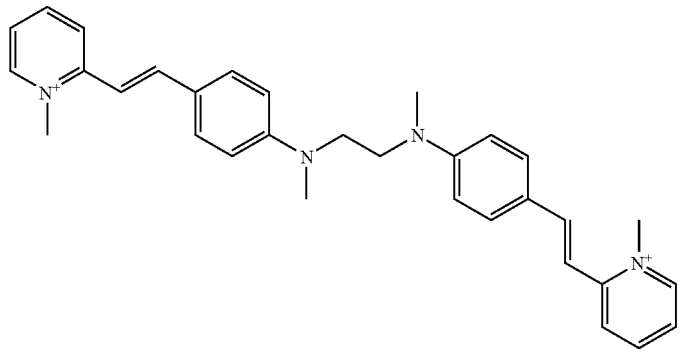

1-methyl-2-[(E)-2-(4-{methyl[2-(methyl{4-[(E)-2-(1-methylpyridinium-2-yl)vinyl]phenyl}amino)ethyl]amino}-phenyl)vinyl]pyridinium dichloride

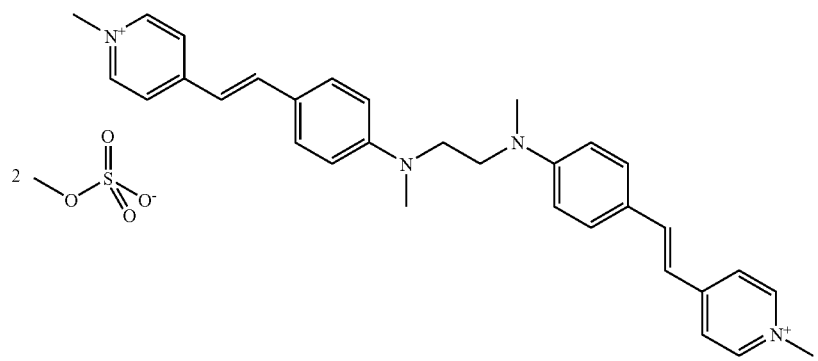

1-methyl-4-[(E)-2-(4-{methyl[2-(methyl{4-[(E)-2-(1-methylpyridinium-4-yl)vinyl]phenyl}amino)ethyl]amino}-phenyl)vinyl]pyridinium bis(methyl sulphate)

-continued

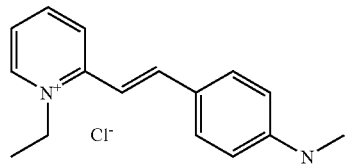

1-ethyl-2-((E)-2-{4-[{4-[{4-[(E)-2-(1-ethylpyridinium-
2-yl)vinyl]phenyl}(methyl)amino]butyl}(methyl)amino]-
phenyl}vinyl)pyridinium dichloride

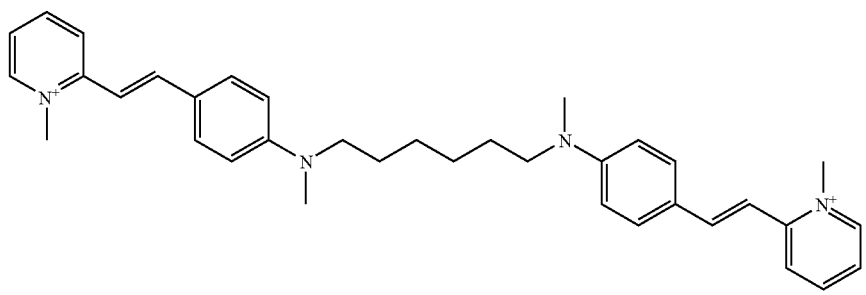

1-methyl-2-[(E)-2-(4-{methyl[2-(methyl{4-[(E)-2-(1-
methylpyridinium-2-yl)vinyl]phenyl}amino)hexyl]amino}-
phenyl)vinyl]pyridinium bis(methyl sulphate)

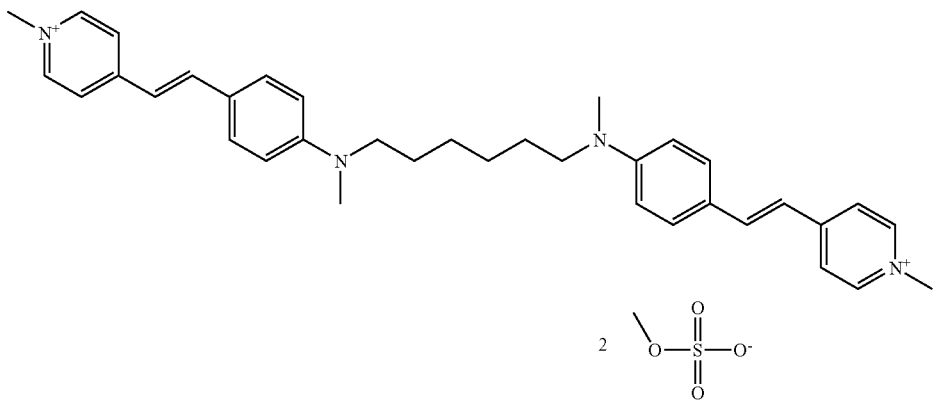

1-methyl-4-[(E)-2-(4-{methyl[2-(methyl{4-[(E)-2-(1-
methylpyridinium-4-yl)vinyl]phenyl}amino)hexyl]amino}-
phenyl)vinyl]pyridinium bis(methyl sulphate).

5. The method according to claim 1, wherein the at least one fluorescent cyanine dye represents from 0.01% to 20% by weight relative to the total weight of the at least one composition.

6. The method according to claim 1, wherein the at least one composition comprises at least one additional fluorescent compound.

7. The method according to claim 6, wherein the at least one additional fluorescent compound represents from 0.05% to 10% by weight relative to the total weight of the at least one composition.

8. The method according to claim 1, wherein the at least one composition comprises at least one additional, non-fluorescent, direct dye.

9. The method according to claim 8, wherein the at least one additional, non-fluorescent, direct dye is chosen from nitrobenzene dyes, azo, azomethine, methine, anthraquinone, naphthoquinone, benzoquinone, phenothiazine, indigoid, xanthene, phenanthridine, phthalocyanine dyes, and the dyes derived from triarylmethane.

10. The method according to claim 8, wherein the at least one additional, non-fluorescent, direct dye represents from 0.0005% to 12% by weight relative to the total weight of the at least one composition.

11. The method according to claim 1, wherein the at least one composition further comprises at least one oxidation base chosen from para-phenylenediamines, bisphenylalkylenediamines, para-aminophenols, orthoaminophenols, heterocyclic bases, and salts thereof.

12. The method according to claim 11, wherein the at least one oxidation base represents from 0.0005% to 12% by weight relative to the total weight of the at least one composition.

13. The method according to claim 1, wherein the at least one composition comprises at least one coupler chosen from meta-phenylenediamines, meta-aminophenols, meta-diphenols, heterocyclic couplers and salts thereof.

14. The method according to claim 13, wherein the at least one coupler represents from 0.0001% to 10% by weight relative to the total weight of the at least one composition.

15. The method according to claim 1, wherein the at least one composition further comprises at least one oxidant.

16. The method according to claim 15, wherein the at least one oxidant is chosen from hydrogen peroxide, urea peroxide, alkali metal bromates, persalts and enzymes.

17. The method according to claim 1, wherein the at least one composition comprises at least one additive chosen from anionic, cationic, nonionic, amphoteric and zwitterionic surfactants, anionic, cationic, nonionic, amphoteric and zwitterionic polymers, organic and inorganic thickeners, antioxidants, penetrants, sequestrants, perfumes, buffers, dispersants, conditioning agents, cationic and amphoteric polymers, modified and non-modified, volatile and non-volatile silicones, chitosans and chitosan derivatives, film formers, ceramides, preservatives, stabilizers and opacifiers.

18. At least one fluorescent dye chosen from compounds of formula (I), compounds of formulae (II), and salts thereof:

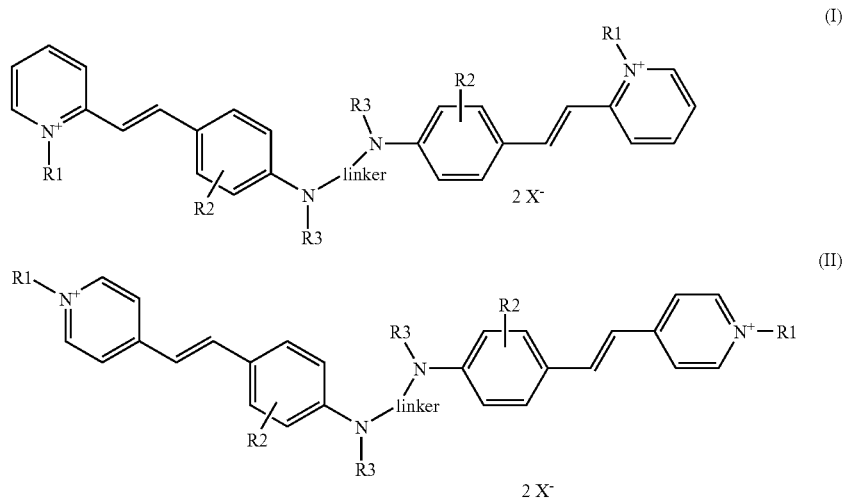

wherein:
linker represents a saturated or unsaturated aliphatic or alicyclic $C_1$-$C_{12}$ hydrocarbon chain, wherein at least one of the carbons of the hydrocarbon chain is optionally replaced by at least one entity chosen from oxygen and NR wherein R is hydrogen or alkyl, and further wherein the hydrocarbon chain comprises no diazo, nitro, nitroso, or peroxide groups, and the hydrocarbon chain terminates at at least one end with a carbon atom;
R1 represents a linear $C_1$-$C_8$ alkyl optionally substituted in a terminal position by hydroxyl or alkoxy;
R2 represents hydrogen; halo; alkyl; alkoxy; amino optionally substituted by at least one $C_1$-$C_4$ alkyl which is optionally substituted by at least one hydroxy;
R3 represents a linear $C_1$-$C_8$ alkyl optionally substituted in a terminal position by hydroxy or alkoxy;
or two R3 form, together with the linker and the nitrogens to which they are attached, a 6- or 7-membered saturated heterocycle of formula:

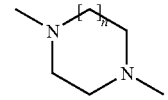

wherein n is 1 or 2; and
X⁻ represents a counterion,
with the proviso that said at least one fluorescent dye is not chosen from 4,4'-{piperazine-1,4-diylbis[4,1-phenyleneethene-2,1-diyl]}bis(1-methylpyridinium) bis (methyl sulphate) and of 4,4'-{1,4-phenylenebis-[methylene(ethylimino)-4, 1-phenyleneethene-2,1-diyl]}-bis (1-methylpyridinium) bis(methyl sulphate), and salts thereof.

19. A cosmetic composition for dyeing human keratin substances with lightening effect, comprising, in a cosmetically acceptable medium, at least one fluorescent cyanine dye chosen from compounds of formula (I), compounds of formula (II), and salts thereof:

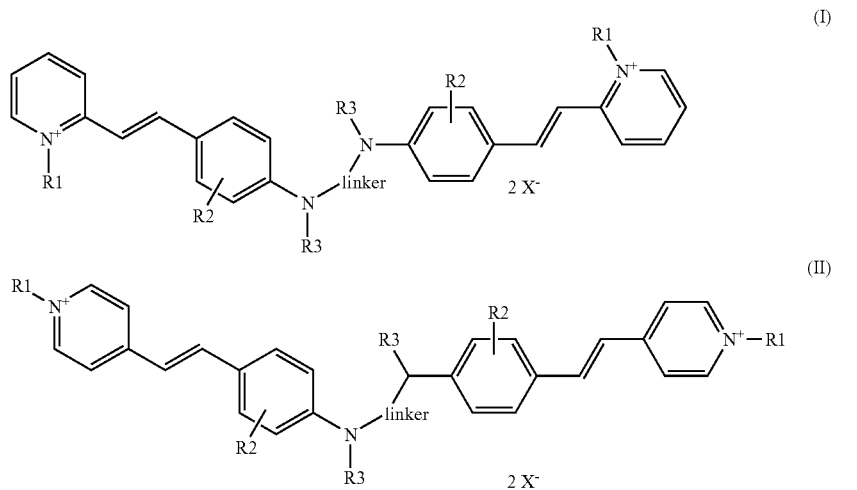

(I)

(II)

wherein:
linker represents a saturated or unsaturated aliphatic or alicyclic $C_1$-$C_{12}$ hydrocarbon chain, wherein at least one of the carbons of the hydrocarbon chain is optionally replaced by at least one entity chosen from oxygen and NR wherein R is hydrogen atom or alkyl, and further wherein the hydrocarbon chain comprises no diazo, nitro, nitroso, or peroxide groups, and the hydrocarbon chain terminates at at least one end with a carbon;

R1 represents a linear $C_1$-$C_8$ alkyl optionally substituted in a terminal position by hydroxy or alkoxy;

R2 represents hydrogen; halo; alkyl; alkoxy; amino optionally substituted by at least one $C_1$-$C_4$ alkyl which is optionally substituted by at least one hydroxyl;

R3 represents a linear $C_1$-$C_8$ alkyl optionally substituted in a terminal position by hydroxy or alkoxy;

or two R3 form, together with the linker and the nitrogen atoms to which they are attached, a 6- or 7-membered saturated heterocycle of formula:

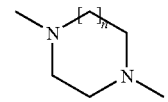

wherein n is 1 or 2; and $X^-$ represents a counterion with the proviso that said at least one fluorescent dye is not chosen from 4,4'-{piperazine-1,4-diylbis-[4,1-phenyleneethene-2,1-diyl]}bis (l-methylpyridinium) bis(methyl sulphate) and of 4,4'-{1,4-phenylenebis-[methylene(ethylimino)-4,1-phenyleneethene-2,1-diyl]}-bis(1-methylpyridinium) bis(methyl sulphate), and salts thereof.

* * * * *